United States Patent [19]

Schmanski

[11] Patent Number: 4,516,069
[45] Date of Patent: May 7, 1985

[54] ELECTROLYSIS TEST STATION TERMINAL AND SUPPORT

[75] Inventor: Donald W. Schmanski, Carson City, Nev.

[73] Assignee: Carsonite International Corporation, Carson City, Nev.

[21] Appl. No.: 481,721

[22] Filed: Apr. 4, 1983

[51] Int. Cl.³ ............................................. G01N 27/00
[52] U.S. Cl. .................................. 324/71.1; 324/425; 156/180
[58] Field of Search ............... 324/71.2, 425, 65 CR, 324/71.1; 156/180; 174/117 F, 117 AS; 339/59 R, 59 M, 113 R

[56] References Cited

U.S. PATENT DOCUMENTS

| | | | |
|---|---|---|---|
| 2,226,928 | 12/1940 | Harvey et al. | 174/117 AS |
| 2,887,721 | 5/1959 | Blanchi et al. | 156/180 |
| 3,015,950 | 1/1962 | Doctor et al. | 324/71.2 |
| 4,219,807 | 8/1980 | Speck et al. | 324/65 CR |
| 4,356,444 | 10/1982 | Saenz, Jr. | 324/425 |

FOREIGN PATENT DOCUMENTS 1390152  4/1975  United Kingdom .

Primary Examiner—Michael J. Tokar
Assistant Examiner—Kevin D. O'Shea

[57] ABSTRACT

An electrolysis test station terminal (10) support for use in connection with measurement of electrical properties of an underground pipe (12). The terminal support includes an elongated web structure (21) formed of nonconductive plastic material and including at least one longitudinal rib (17, 18, 19) integrally formed as part of the web structure. A hollow core (30, 31, 32) is formed within the longitudinal rib and provides a housing for conductive wire (37, 38) to be concealed therein. An opening in the longitudinal rib provides access to the core to enable physical contact (37a, 38a) for measurement of electrical properties as conducted from the underground pipe through the wire into the terminal support.

15 Claims, 5 Drawing Figures

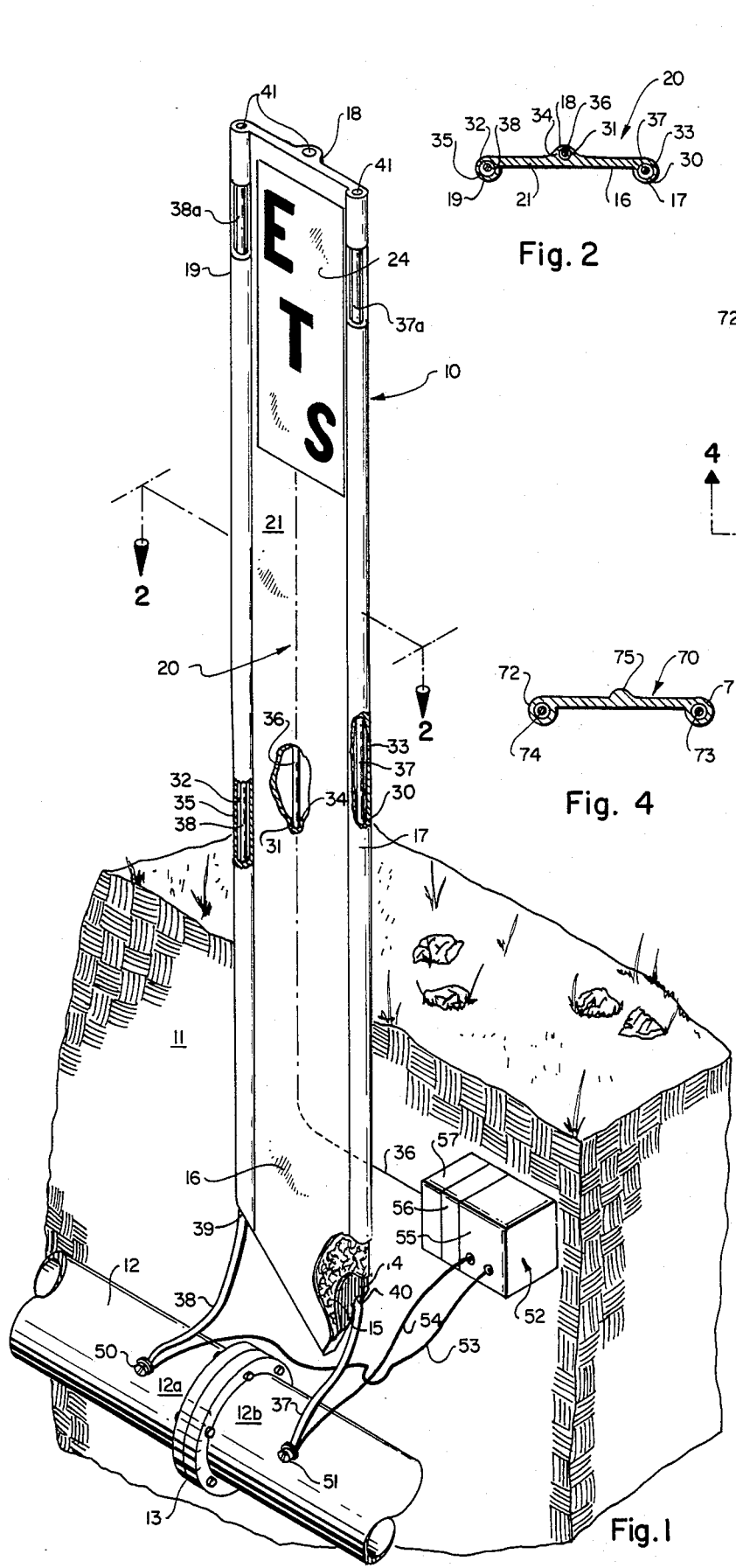
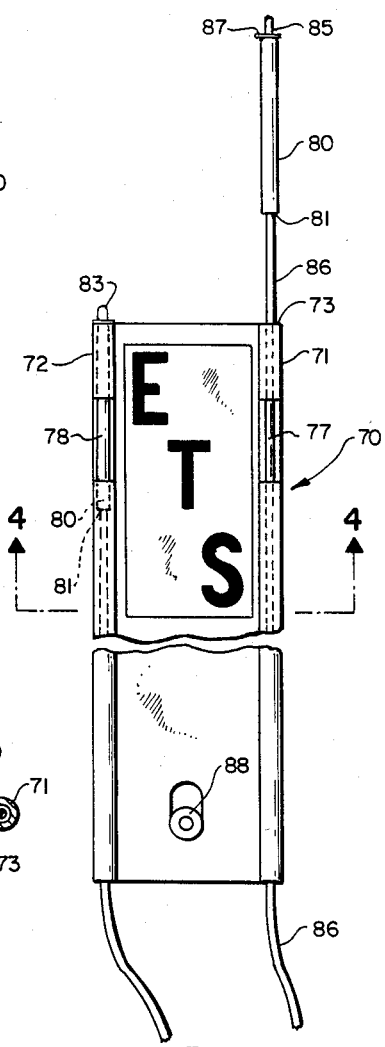
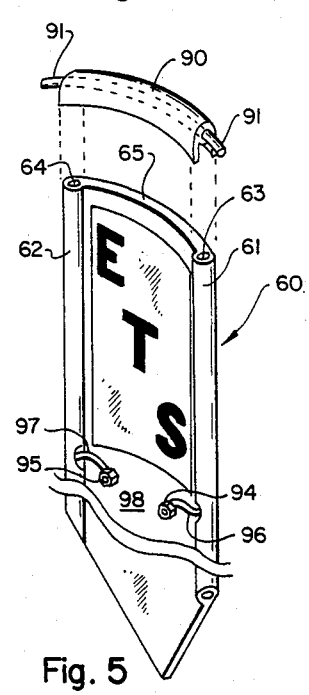
Fig. 1
Fig. 2
Fig. 3
Fig. 4
Fig. 5

ELECTROLYSIS TEST STATION TERMINAL AND SUPPORT

BACKGROUND

1. Field of the Invention

This invention pertains to devices used in connection with the detection and measurement of the electrical environment of buried metallic pipelines which become subject to the destructive effects of corrosion. More specifically, the present invention pertains to an electrolysis test station terminal assembly which provides insulation, protection and support for conductive wires coupled to the underground pipe and reference electrodes or ground contacts, and is positioned by means of the subject invention to an above-ground orientation in plain view and with exposed terminal leads for direct measurement.

2. Prior Art

The corrosive destruction of expensive underground pipe systems continues to create serious problems for virtually all industries utilizing underground conduit. For example, the telephone industry, power and light industry, gas and oil industry, and many other similar industries rely heavily on buried pipelines to convey and protect fuels, cables, and other materials. In view of the substantial expense related to underground pipeline construction and subsequent repair efforts where such pipeline is damaged, continuous attention has been applied to reduce and detect corrosion activity.

Although corrosion may result from numerous types of chemical reactions and environments, buried metallic pipelines are particularly subject to electrochemical corrosion. Two specific categories of electrochemical corrosion include (i) galvanic and (ii) straight current corrosion. In the case of galvanic corrosion, a current flow is established between discrete areas of oxidation and reduction reactions at the buried pipeline. Such galvanic currents are the effect of corrosion activity and provide means for electrical detection of corrosion by current measurement. A common source of galvanic corrosion occurs when a differential aeration corrosion cell is established on the metallic surface of an underground pipe in contact with an electrolyte.

In addition to development of current by reason of oxidation reduction reactions in the corrosion process, current may also develop from stray sources foreign to the affected pipeline. Such stray currents unusually occur in metropolitan environments where intense earth voltage gradients may exist, such as from a direct-current railway system or nearby impressed current cathodic protection anode bed. The underground pipe surface receiving current where the earth voltage is more positive is protected from corrosion. On the other hand, if earth voltage is less positive, the metallic surface acts as an anode and is subject to corrosion reaction.

Prior art methods of solving the corrosion problem resulting from electrochemical causes have included treatment of the cause as well as the effect of the reaction. Solutions have included coating the metallic pipes with insulative materials which operate as a barrier to current flow. Other protective coatings are utilized to establish an insulative barrier between electrolyte within the underground soil and the metallic surface of the pipe. Such coatings range from coal tar enamel coatings, asbestos felt, and polymer coatings.

In addition to protective coatings, sacrificial anodes may be buried for purposes of preferential reaction by reason of stray current which could otherwise attack the metallic substance of the buried pipe. Pieces of magnesium, for example, may be buried under the earth at underground sites which are likely to present likelihood of corrosive attack.

It will be apparent that ongoing measurement of current and/or voltage in the pipe vicinity is required to verify that the protective coatings over pipe surfaces or adjacent sacrificial anodes are properly operating. For example, the presence of galvanic current near the surface of a coated pipe would indicate corrosive action and a likely break in the coating material. Similarly, a change in current flow in an environment with a sacrificial anode can indicate changed conditions which would require other preventive action.

Accordingly, it has been well-known to implace test leads at the pipe surface, ground potential sites, or other underground electrical points of interest and to maintain a program of periodic measurement of current or voltage potential in order to identify possible corrosion activity.

In addition, the measurement of pipe potential to its environment at regular intervals helps to identify the more corrosion-active areas. Accordingly, when a pipe is buried, electrolysis test stations or terminals will be established with leads being coupled from the underground detection points (pipe, sacrificial anode, electrolyte concentrate, etc.) to a ground level test station having terminals for direct voltage or current measurement. These measurements are manually taken by utility personnel at each test station location.

Gas, electric, telephone and water utilities have utilized such measurement techniques for many years as part of a cathodic protection program for detection or prevention of corrosion. Typically, such measurements are taken at a ground level test station which comprises a flat terminal board enclosed in a rigid, protective encasement. This casement is usually cylindrical in form, with a top cover to protect the terminal and attached leads from damage. These leads are coupled by conductive wire to various test points along the pipe length, as well as other sites of interest.

Several problems arise with the present types of test stations. Where the terminal encasement is below ground level, its location may be difficult to find. In urban areas, locations are typically mapped and are exposed on sidewalk or road surfaces. Except for problems arising from vandalism, such ground level test stations provide the desired protection and access for measuring current and voltage at underground pipes.

In a rural setting, however, underground pipelines traverse fields, open terrain, and other areas where vegetation, earth and other natural cover may conceal the test station location. It will be apparent that much of the underground pipeline of utilities spans distances between cities and even states and is subject to a variety of soil conditions which create the need for some form of cathodic protection.

In order to deal with the problem of identification and location of terminal test stations, above-ground terminals have been developed which are similarly constructed of an outer protective encasement which encloses the terminal and attached leads. Such above-ground test stations have a rigid cylindrical or tubular body, customarily fabricated from strong plastics, such as a glass-filled polycarbonate. These tubular structures are rigid, column-like structures which are intended to have a sufficiently high profile to be identifiable to maintenance personnel. This high profile, tubular structure follows the pattern of cylindrical encasements which have been used for many years in ground level test stations.

The above-ground test station is even more vulnerable to vandalism problems, however, than was its ground level counterpart. This is true because the structure is recognizeably distinct as a test station and represents a high profile target for destruction by vandals. In addition to losses from vandalism, damage to the tubular structure and contained terminal is frequently caused by roaming animals and farm equipment. For example, tractors and cross-country vehicles can quickly destroy such terminal stations upon impact.

Therefore, the industry is faced with the dilemma of choosing between low-risk ground level detection stations (which are very difficult to locate) or highly vulnerable above-ground test stations subject to damage from vandals, animals, and farm equipment. In view of the cost of labor and travel associated with locating a ground level system of test stations, this choice is usually biased in favor of the vulnerable above-ground devices as described. Accordingly, the utility industries and public must bear the cost of repeated replacement and repair of the above-ground terminal test station. The accepted strategy for minimizing test station damage appears to be to reinforce and strengthen the encasement to rigidly resist effects of damaging influences.

What is needed, therefore, is an improved cathodic protection or electrolysis test station (referred to hereafter as ETS) which as a high, visible profile suitable for easy identification, yet does not draw attention and is capable of surviving the impact or contact with vandals, vehicles, or roving animals.

SUMMARY AND OBJECTS OF THE INVENTION

It is therefore an object of the present invention to provide a high profile ETS terminal support particularly adapted for rural applications and capable of surviving violent contacts with animals and equipment.

It is a further object of this invention to provide an ETS terminal support having a singular structure which facilitates quick installation and discourages disassembly, pilfering and other attacks of vandalism.

It is an additional object of this invention to provide an ETS terminal support whose structure merely resembles a post without an appearance of enclosed contents, suggesting de minimis value.

A still further object of this invention is to provide an ETS terminal support which is a unibody structure requiring no assembly, and being capable of deflection and restoration to an upright position subsequent to impact.

A still further object of the subject invention is development of an ETS terminal support wherein the test leads remain permanently exposed for contact and measurement, without the need for entering an encasement or other enclosing device.

It is yet another object of the present invention to provide a structure which functions as an ETS terminal support, as well as an encasement for an antenna associated with a telemetry unit utilized for transmitting specified signals in connection with cathodic protection and measurement.

These and other objects are realized in an electrolysis test station terminal support suitable for use in connection with measurement of voltage differences and/or current flow between underground pipe, ground potential or other electrical parameters associated with cathodic protection. The ETS terminal support includes a single, elongated, unitary structure formed of an impact-resistant, flexible, resilient, electrically-nonconductive plastic material. This structure is formed with sufficient length and rigidity to enable implacement of a bottom portion thereof below ground level and a top portion thereof above ground level in a stable, vertical orientation. The terminal support is formed with a thin web section along its length to improve flexibility and with a width greater than approximately five centimeters to provide sufficient surface area for attachment of identification information at the top thereof. At least one longitudinal rib is integrally formed as part of the single unitary structure and extends from the top portion to the bottom portion thereof. This rib is characterized by a hollow core along its length having a diameter sufficiently large for enclosure of a portion of a conductive wire therein which is to be coupled to electrical testing sites at the pipe surface or other electrical points of interest. The rib wall thickness around the core assists in providing rigidity and impact-resistance to the elongated structure. Openings are provided in the bottom and top portions of the rib to permit insertion of the conductive wire into the core and to provide direct physical access to such inserted wire at the upper portion of the rib structure. The rib core and upper coating can be so constructed so as to receive a conductive tube adapted for a tight fit within the upper core. This tube may have a conductive, metallic cap which adapts the tube for full insertion into the upper rib core, with the cap seated at the top of the terminal support. This cap may serve as a measurement lead for an electrically coupled wire leading to the buried pipe surface or other point of electrical interest. In addition, a lateral opening in the rib wall structure can be provided for additional physical access to the tube and coupled wire.

The subject invention provides a flexible, impact-resistant, unitary structure which performs all of the functions of prior art test stations in a cathodic protection system. In addition, the structure provides high profile for easy detection, yet gives an appearance of de minimis value to discourage vandalism. In addition, the structure is easily adapted for telemetry use, as well as providing multiple test lead points.

DETAILED DESCRIPTION OF THE DRAWINGS

FIG. 1 shows a perspective view of an electrolysis test station terminal and support constructed in accordance with the teachings of the present invention.

FIG. 2 shows a cross-section of the terminal and support of FIG. 1, taken along the lines 2—2.

FIG. 3 shows a segmented plan view of the upper and lower portions of a different embodiment of the subject invention having a central rib for increased strength and rigidity, and lateral ribs for housing test leads.

FIG. 4 represents a cross-section of the embodiment of FIG. 3 taken along the lines 4—4.

FIG. 5 shows a segmented, perspective view of a concave-convex configuration of the subject invention representing the upper and lower portions, with a shunt cap illustrated in disconnected manner.

DETAILED DESCRIPTION OF THE INVENTION

Referring now to the drawings:

An electrolysis test station (ETS) terminal support 10 is shown generally in FIG. 1. It is positioned in the ground 11 or other location near a metallic pipe 12 which has been buried. The pipe, in this instance, is shown with a flanged coupling 13 wherein the respective segments of the pipe 12a and 12b are electrically insulated from each other.

The ETS terminal support 10 is a single, elongated, unitary structure formed of an impact-resistant, flexible, resilient, electrically non-conductive plastic material. In the preferred embodiment, the single, unitary structure is fabricated by the pultrusion process, wherein reinforcing fibers are conducted through a resin bath and die cavity to harden the resin/fiber composite into a rigid structure. For the embodiment 10 shown in FIG. 1, the die cavity opening through which the resin/fiber composite is conducted and solidified is represented by the perimeter configuration of the cross-section 20 shown in FIG. 2.

Many combinations of fibers can be utilized to realize the structure claimed as the subject invention. As an illustration of one combination, the terminal support 10 shown in FIG. 1 includes longitudinal fiber or roving 14 which is loaded in the rib sections 17, 18, and 19 of the pultruded body 20. This longitudinal fiber operates to give increased longitudinal rigidity and impact resistance to the unitary structure 20 formed in the pultrusion process.

In addition to the rib structure 17, 18, and 19 of the pultruded body 20, a web section 21 is formed as an integral part of the overall structure by feeding a fabric 15, such as cross-weave or random mat (as shown in FIG. 1) through the pultrusion die cavity in combination with the roving 14 and impregnated resin which forms the balance of solid structure binding the respective fibers into the single, unitary composite. Because of the thinner dimension of the web section 21, improved flexibility is provided to the elongated structure 20, while increased strength is rendered by the multi-directional fabric 15 which ties the web and rib structure together into a single composite material.

A surface fabric 16 such as remay is utilized to give a finished appearance to the structure. These various components of a composite structure formed by the pultrusion process are commercially available in many equivalent forms and actual fabrication procedures are well-known to those skilled in the art of pultrusion. Therefore, further explanation is deemed unnecessary with respect to actual fabrication of a pultruded composite.

Fabrication of the subject elongated structure is not limited to fiber reinforced composites, nor to the pultrusion process. Non-reinforced plastic structures may be manufactured using well-known processes such as extrusion or injection molding to obtain the desired unitary, integral structure for the subject invention.

Although resin compositions applied in the pultrusion art are typically thermosetting resins of various formulae, thermoplastic resins may likewise be applied as the material composition for the subject structure, and may be either reinforced or nonreinforced. It will be apparent to those skilled in the art of plastics that structural characteristics of strength, resilience, impact-resistance, and flexibility will depend upon the nature of plastic selected, and its method of fabrication. The addition of reinforcing fibers will further enhance strength, impact resistance, and column rigidity. In summary, therefore, the composition of the subject elongated, unitary structure may be of a thermoplastic or thermosetting resin, either reinforced or non-reinforced, depending upon desired design characteristics of strength, impact resistance, column rigidity, flexibility, and resilience.

The embodiment illustrated in FIG. 1 can be generally characterized as a glass-reinforced polyester composite. Where less impact resistance is required, polyvinyl chloride compositions may be utilized. Polycarbonate, either reinforced or non-reinforced, may also be utilized to give increased impact resistance over the polyvinyl chloride material.

In selecting the specific polymer compositions to be utilized, it is essential that the electroconductivity of such polymer fall within the general classification of insulative or non-conductive materials. This insulative character is essential for electrical isolation of contact leads and coupled conductive wire which provide measurements of voltage differences, current flow, etc. (Conductive plastic materials would not be suitable in view of shunting effect of such plastics between contacted leads or conductive wire which is encased within the elongated structure.

By utilizing insulative materials, the effective operation of the ETS terminal support is maximized. Specifically, voltage measurements are more accurate, wire leads are protected from electrical contact with other leads in a multiple test station configuration. In addition, further encasement of conductive wires within the elongated, insulative body of the terminal support 10 protects measurements against external electrical influences which may adversely affect the test station.

The previous general reference to unitary structure (such as is characterized by a pultruded composite) has reference to any structure whose claimed elements are integrally formed as part of a single body. Such unitary structures are generally formed by a single manufacturing operation such as pultrusion, extrusion, injection molding, or the like. This structure not only enhances cost effectiveness of the terminal support, but simplifies assembly, installation, and related labor costs.

In the context of the present invention, an even more unusual and surprising aspect of the unitary structure is the indirect discouragement of vandalism. Inasmuch as the unitary structure presents an impression of something having de minimus value, and whereas the appearance does not suggest parts which can be disassembled, removed, or otherwise disposed of, a potential vandal is discouraged from wasting time with this type of item. Furthermore, removal of the elongated, unitary structure, when properly installed to a sufficient depth in the soil (at least one foot), is extremely difficult to extract without special tools. Hence, the terminal support 10 is ignored much like a fencepost or other type of pole buried in the ground.

The length of the terminal support 10 will vary, depending upon the terrain to which it is to be applied. Obviously, where dense vegetation exists, the terminal support must be sufficiently high to permit visual identification over the foliage. The length should be sufficient to enable emplacement of a bottom portion of the structure to be implanted below ground level. Furthermore, the structure must have sufficient length and rigidity to provide a stable orientation for a top portion thereof to be positioned in a stable, vertical orientation. It is apparent that the longitudinal rigidity of the top portion will depend upon the material composition and the length of exposed terminal support structure, along with the geometric cross-section and moment of inertia thereof.

As previously indicated, the elongated structure 20 includes a web section 21 which extends along its length and at least one longitudinal rib 17, 18, or 19. The width of the terminal support is primarily determined by the width of the web section 21, which may be considered to extend into any laterally disposed rib structure (i.e., 17 and 19). Generally speaking, the web section width will be at least five centimeters in order to provide sufficient surface area for attachment of identification means 24 at the top portion thereof. Here again, width will vary, depending upon the specific environment in which the terminal support is to be used. Generally, at least five centimeters width will be necessary to ensure sufficient longitudinal rigidity, identification surface, and silhouette visibility for easy perception by maintenance personnel looking for the structure. The various terminal support structures illustrated in the figures have widths of approximately nine to ten centimeters, giving greater stiffness to the upright structure and increased silhouette for easy perception.

The rib structure 17, 18 and 19 of the terminal support shown in FIG. 1 extends from the top portion to the bottom portion of the terminal support. Although such rib structure need not extend the full length of the web section 20, fabrication processes such as pultrusion will generally yield common lenghts of web and rib structure.

Each of the rib sections 17, 18 and 19 in FIG. 1 include a hollow core 30, 31 and 32 whose inner diameter is sufficiently large to house a conductive wire whose size is compatible for use as a connecting wire to the underground pipe 12. The core is formed within the pultruded rib structure by a unique technique utilizing standard pultrusion equipment. The pultrusion method is supplemented by the use of a core fabrication method wherein an elastic strand of circular cross-section is pulled with the roving 14 through the thermal setting die cavity with the roving and resin suspended around the rubber strand. As the composite material is solidified, the rubber strand occupies the volume which is intended to be the core within the rib structure. The core is readily formed by stripping the rubber strand from its enclosed position within the hardened rib structure. The rubber strand is easily freed from the enclosing composite material because as it is stretched, its cross-section decreases and separates from the interior surface of the ribbed wall 33, 34 and 35. Other methods could be utilized to form the core, such as suspending a steel mandrel in a proper position centrally in each of the rib areas 17, 18 and 19 in the cross-section shown in FIG. 2 representing the die cavity geometry. The roving and resin are then drawn around the mandrel in a conventional manner, leaving the solidified rib with open core structure.

Obviously, the diameter of the core may vary, depending upon the core function. For example, the central core 31 is shown to house an antenna 36 which may be used in connection with telemetry signals to be broadcast from the test station. On the other hand, side ribs 17 and 19 contain heavy-duty wire 37 and 38 which is coupled to the underground pipe 12 for electrical monitoring. In the latter case, the rib core must be larger to provide the necessary space required for the larger conductive wire 37 and 38.

Although it is possible to merely form uniform core diameters which are capable of containing the larger sized wire, regardless of whether the core is to be used for a thin antenna wire or some other purpose, it is desirable to maintain the core diameter at its lowest possible value to thereby permit greater wall thickness in the rib structure 17, 18 and 19.

It will be apparent that the thickness of rib wall 33, 34 and 35 around each core directly affects the impact resistance and rigidity of the rib structure. It is desirable, therefore, that the longitudinal rib have sufficient wall thickness around the core opening to maintain the longitudinal rigidity and impact resistance of the elongated structure 10. For example, the central rib 18 may be formed with a smaller core to provide an increased amount of glass roving and resin for strengthening the structure against destructive impact.

A primary function of the associated rib and core structure is to conceal the conductive wire or antenna from view and to limit access. Instead, the present structure gives an appearance of a mere post or marker having no apparent material value which might arouse the curiosity of a potential vandal.

The only openings within the wall structure of the rib would be to provide physical access to the contained wire 37a and 38a to enable contact for voltage or current measurement. Typically, this would be accomplished by a service man applying an appropriate contact at each exposed surface 37 and 38 to identify the electrical activity of the underground pipe, represented by sections 12a and 12b. Such openings need not be large and would therefore not alert vandals to the nature and value of the ETS terminal.

Naturally, access openings 39 and 40 are required at the base of the terminal support 10 so that wires 37 and 38 coupled to the underground pipe 12 can be received into the terminal support as shown. Likewise, an opening would be required for the central antenna wire 36.

To discourage removal of the terminal structure from around the contained wires, soldered or welded caps 41 can be coupled to each wire 36, 37 and 38, having a cross-section larger than the core diameter to prevent the wire from further receding into the core structure. These respective heads can also be utilized as terminal contact points or for shunting two or more wires in combination, as is shown in FIG. 5. Such contacts may be in place of or in addition to lateral openings which expose wire segments 37a and 38a for electrical measurement.

It should be noted that the subject invention is not dependent upon any specific type of voltage or current measurement or associated electrical system. The terminal support functions to provide a protective and concealing structure for electrical contacts which may be associated with numerous types of electrical test stations. In addition to the concealing function, the subject structure enables quick access for measurement, without presenting structure which attracts the attention of vandals or which is susceptible to breakage by roving animals or vehicles.

As an illustration of one of numerous types of electrical test station applications of the subject invention, FIG. 1 illustrates contacts 50 and 51 which electrically couple wires 37 and 38 to underground sections of pipe 12a and 12b. These pipe sections are electrically insulated by a coupling flange 13. Wires 37 and 38 permit direct measurement of voltage difference between the respective underground pipe sections, which can be readily measured at 37a and 38a.

A telemetry unit 52 may be added to the ETS to provide automatic signals which alert a utility company to an unsafe condition based on the voltage difference between pipe sections 12a and 12b. As shown, contact leads 53 and 54 are coupled at pipe contacts 50 and 51, enabling a monitoring device 55 to constantly measure voltage differences. Detection circuitry 56 is coupled to the monitor 55 for actuating a telemetry circuit 57 when voltage differences exceed a predetermined value. When operating, the telemetry circuit 57 emits a signal into the antenna 36 which is housed in the central rib 18 of the terminal support shown. The signals are broadcast through the terminal support, providing appropriate notice to the utility company.

It will be apparent to those skilled in the art that numerous variations may be applied to the terminal support invention disclosed. For example, additional wire and detection sites may be added by additional rib/core structure in intermediate positions between the side ribs 17 and 19. Where added strength is needed, solid core ribs may be used.

Likewise, the specific geometry of the web section is not critical, provided its cross-section and associated moment of inertia provide a flexible and resilient structure, based on the composition of matter used. For example, FIG. 5 illustrates an arcuate terminal support 60 with lateral ribs 61 and 62, each having a hollow core 63 and 64. This current structure enables the use of rigid materials such as fiber-reinforced composites which can flex in a sufficiently large bending radius to avoid localized fracture and loss of resilience. It will be apparent that numerous combinations of geometry and material stiffness and resilience can be applied to develop the subject terminal support which gives the appearance of a substantially flat marker of de minimus value.

FIG. 3 discloses additional structure for protecting enclosed conductive wire and facilitating quick access for electrical measurements. The terminal support 70 has laterally extending ribs 71 and 72, each having a core 73 and 74 in each lateral rib. A third rib 75 has a solid core to increase the strength and resilience. Each hollow core extends along the lateral ribs to the top end of the structure. Rib wall structure is removed just below the top end to provide measurement terminals 77 and 78.

Terminals are formed at each lateral rib core utilizing an electrically conductive tube 80 having a cross-sectional shape conforming to the cross-sectional shape of the hollow core 73 and having a diameter slightly smaller than the core diameter to provide a close fit of the tube within the core as shown in rib 72. The length of the tube 80 is greater than the distance from the top end of the terminal support 70 to the lowest part of the lateral opening 77. This operates to conceal the base end 81 of the conductive tube 80 within the concealment of the rib core.

A cap means 83 is coupled to the top of the conductive tube and has a diameter greater than the core diameter to retain the cap outside the core and the tube in a position at the top end of the rib with a lower portion of the tube surface exposed through the lateral opening 78. This cap can be formed by soldering the free end 85 of the conductive wire 86 with the top end 87 of the conductive tube. This permanently connects the wire 86 and tube 80 with a rounded head such as shown in 83.

This terminal structure is preferable over merely exposing the conductive wire 86 by providing protection for the soft copper metal which would otherwise be physically accessible through openings 77 and 78. The tube can be made of stronger metal such as tin, steel, or the like.

In this configuration, the combined conductive tube 80 and wire 86 provide a single electrical path from the top 73 of the terminal support past the base of the support for attachment to an underground pipe. This terminal support 70 includes a tubular retainer 88 which operates to anchor the terminal support when buried in the ground.

FIG. 5 illustrates the use of a shunt 90 having a conductive coupling 91 which seats against a pair of terminal heads (not shown) which would project through the core openings 63 and 64.

Where a shunt cap is not necessary, the conductive element 91 can be omitted and the structure of the cap extended or enlarged to conceal the top cross-section 65 of the terminal support.

With the configuration shown in FIG. 3, a cap can be structured with a recess sufficiently deep to cover both the top terminal leads 83 and 85, as well as the lateral access contacts 77 and 78.

As an alternative to lateral openings as shown at 77 and 78 in FIG. 3, terminal leads can be exposed as shown in FIG. 5 with nut and bolt mounts 94 and 95. These bolts serve as means for retaining the exposed terminal contact leads 96 and 97 at the web surface 98 of the terminal support 60.

It will be apparent to those skilled in the art that other embodiments and modifications to the present disclosure can be made without departing from the inventive subject matter as defined by the following claims.

I claim:

1. An electrolysis test station terminal support for use in connection with measurement of voltage difference and/or current flow between an underground pipe and ground potential, said terminal support comprising:

a single, elongated, unitary structure formed of an impact-resistant, flexible, resilient, electrically non-conductive plastic material and having sufficient length and rigidity to enable implacement of a bottom portion of said structure below ground level and a top portion thereof above ground level in a stable, vertical orientation;

said structure being substantially comprised of a thin web section along its length to improve flexibility and having a width greater than approximately 5.0 cm to provide sufficient surface area for attachment of identification means at the top portion thereof;

said structure further including at least one longitudinal rib integrally formed as part of the single unitary structure and extending from the top portion to the bottom portion, said rib having a hollow core whose diameter is sufficiently large to house a conductive wire adapted for use as connecting wire to the underground pipe; and said longitudinal rib having sufficient wall thickness around said core to maintain the longitudinal rigidity and impact-resistance of the elongated structure, said wall structure including an opening in the bottom portion thereof to permit insertion of the conductive wire into said core, and further having an opening in the top portion of said wall structure to provide physical access to said wire when inserted therein to enable contact for voltage or current measurement.

2. A terminal support as defined in claim 1 wherein the rib extends to the top end of said structure, said hollow core likewise extending to the same top end such that the core hollow is exposed to view along its longitudinal axis, said wall structure of the rib being partially cut away below the top end to form a lateral opening operable as said top opening to provide physical access for voltage or current measurement, said terminal support further comprising:
- an electrically conductive tube having a cross-sectional shape conforming to the cross-sectional shape of the hollow core and having a diameter slightly smaller than said core diameter to provide a close fit of said tube within the core, said tube having a length greater than the distance from the top end of the elongated structure to the lowest part of the lateral opening in the rib wall structure; and
- cap means coupled to the top of the conductive tube and having a diameter greater than the core diameter to retain the cap outside the core and the tube in a position at the top end of the rib with a portion of tube surface exposed through said lateral opening.

3. A terminal support as defined in claim 2, further comprising a conductive wire seated within and electrically coupled to said conductive tube, and extending therefrom through the length of the hollow core of the rib in concealed manner, said wire having sufficient length to extend substantially beyond the opening in the bottom portion of the elongated structure to provide means for electrical contact with said pipe, ground potential, or other desired point of electrical contact.

4. A terminal support comprising at least two longitudinal ribs and tube-mounted, conductive wires in accordance with the structure of claim 3, said structure further comprising a removable shunt cap coupled to at least two of the conductive tubes to develop a temporary closed circuit therebetween.

5. A terminal support as defined in claim 1, further comprising means for retaining an exposed terminal contact lead at the top portion of the terminal support to thereby enable detection of electric signals.

6. A terminal support as defined in claim 5, wherein said means for retaining the exposed terminal contact lead comprises a nut and bolt combination anchored at opposing sides of the web at the top portion of the elongated structure and in close proximity to the wall structure opening at the top portion of said rib.

7. A terminal support as defined in claim 1, further comprising a plurality of longitudinal ribs integrally formed as part of the single unitary structure, each rib having a hollow core therein, thereby adapting said structure with a plurality of rib enclosures for multiple conductive wires.

8. A terminal support as defined in claim 1, wherein the elongated structure comprises a web section bound at each side by a longitudinal rib integrally formed with said elongated structure and having a hollow core therein as defined in claim 1;
said elongated structure further comprising a third longitudinal rib integrally formed with said web and having a solid core and a sufficiently high modulus of elasticity to provide longitudinal rigidity to the terminal support.

9. A terminal support as defined in claim 1 wherein the web section is configured with a concave-convex cross-section to enhance longitudinal rigidity.

10. A terminal support as defined in claim 1, further comprising a conductive wire positioned within said hollow core at said longitudinal rib, said wire extending to the opening in the top portion of the rib wall structure and including means for attaching an exposed end thereof to the web section as a terminal contact lead, the other end of the wire extending through the opening in the bottom portion of the rib wall structure and having sufficient length for attachment to a voltage measurement source.

11. A terminal support as defined in claim 1 wherein the plastic material comprises a thermoplastic resin and includes fiber-reinforcement in an appropriately balanced ratio of longitudinal roving and fabric fibers to provide the required impact resistance, flexibility and resilience.

12. A terminal support as defined in claim 1, further comprising an additional longitudinal rib integrally formed with said elongated structure and having a hollow core therein adapted for housing an antenna capable of transmitting a radio signal from said terminal support.

13. A terminal support as defined in claim 12, further comprising detection means for detecting the occurrence of a specific electrical condition; signal means coupled to said detection means for developing a signal indicating the occurrence of said condition; telemetry means coupled to said signal means for receiving and transmitting a radio signal indicating the occurrence of said condition and an elongated antenna concealed with the hollow core as defined in claim 14 and coupled to said telemetry means for broadcasting the telemetry signal.

14. A terminal support as defined in claim 13 wherein said detection means is attached to an underground pipe and said signal and telemetry means are buried underground in a protective casing, providing a fully-concealed detection and telemetry system, except for the terminal support which projects above ground with the concealed antenna.

15. A method of fabricating a terminal support as defined in claim 1, wherein the device is formed by the pultrusion process in accordance with the following known steps:
(a) passing a combination of fabric and roving fibers through a resin bath;
(b) conducting the coated fibers through coordinated gates and guides for properly aligning the fibers for selective induction into a die cross-section to obtain a predetermined, hardened laminant structure;
(c) passing the aligned fibers through a heated die for curing the resin matrix into said hardened structure, the improvement comprising the additional steps of passing an elastic strand through the gates and guides with the coated fiber, said strand being pulled through the die cavity with the roving and resin suspended around the strand such that the strand occupies the volume which is intended to be the core within the hardened rib structure; and
(d) stripping the strand from the hardened laminate structure to form the core void.

* * * * *